United States Patent [19]

Andresen et al.

[11] Patent Number: 4,708,782
[45] Date of Patent: Nov. 24, 1987

[54] CHROMATOGRAPHY COLUMN-ELECTROPHORESIS SYSTEM

[75] Inventors: Brian D. Andresen, Pleasanton; Vinit Saxena, Pinole, both of Calif.

[73] Assignee: Sepragen Corporation, San Leandro, Calif.

[21] Appl. No.: 906,846

[22] Filed: Sep. 15, 1986

[51] Int. Cl.[4] .................... G01N 27/26; G01N 30/72; B01D 15/08; H01J 49/00
[52] U.S. Cl. .................... 204/299 R; 204/180.1; 250/288; 422/70; 436/161; 436/173; 210/198.2; 210/198.3; 210/656; 210/658
[58] Field of Search .................... 204/299 R, 180.1; 250/288, 288 R, 288 A; 210/198.2, 198.3, 656, 658, 659; 422/70; 436/161, 173

[56] References Cited

U.S. PATENT DOCUMENTS

| | | | |
|---|---|---|---|
| 3,997,298 | 12/1976 | McLafferty et al. | 210/198.2 X |
| 4,055,987 | 11/1977 | McFadden | 210/198.2 X |
| 4,391,778 | 7/1983 | Andersen et al. | 422/70 X |
| 4,501,817 | 2/1985 | Andresen et al. | 436/161 |

OTHER PUBLICATIONS

C. R. Blakley and M. L. Vestal, "Thermospray Interface for Liquid Chromatography/Mass Spectrometry", Anal. Chem. 55, 750–754 (1983).
Patrick V. Arpino et al, "Optimization of the Instrumental Parameters of a Combined Liquid Chromatograph–Mass Spectrometer, Coupled by an Interface for Direct Liquid Introduction, Journal of Chromatography 203, 117–130 (1981).
José A. Olivares et al, "On-Line Mass Spectrometric Detection for Capillary Zone Electrophoresis", Analytical Chemistry, vol. 59, No. 8, Apr. 15, 1987.

Primary Examiner—John F. Niebling
Assistant Examiner—John S. Starsiak, Jr.
Attorney, Agent, or Firm—Shyamala T. Rajender

[57] ABSTRACT

A chromatography column-electrophoresis system for directing the fluid output from the column directly to a point of use, further resolution or separation, detection and/or identification while conditioning or preparing the output for analysis by another instrument such as a mass spectrometer. The system provides for substantially simultaneous analysis in a mass spectrometer, for example, material separated initially by the column, followed by electrophoretic separation and resolution. The chromatography column utilizes horizontal or radial flow of the sample fluid through the separating medium. The column may be of a type having a quickly replaceable or disposable separating medium, or the entire column may be of a readily replaceable or disposable type. The electrophoresis apparatus is of a capillary tube type, one embodiment of which utilizes a pair of capillary tubes thereby providing for continuous operation.

22 Claims, 5 Drawing Figures

CHROMATOGRAPHY COLUMN-ELECTROPHORESIS SYSTEM

BACKGROUND OF THE INVENTION

The present invention relates to systems for separating a sample fluid in a liquid chromatography column and directing the effluent from the column to a point of use, or point of further separation or detection and identification, particularly to a combination of a chromatography column and an electrophoresis apparatus for directing and conditioning the effluent for further analysis and still more particularly to a combination of a horizontal or radial flow chromatographic column and an electrophoresis apparatus utilizing at least one capillary tube and a valving arrangement for controlling the column effluent and buffer material passing therethrough.

In a liquid chromatography system, a sample fluid, followed by an elution fluid are injected into a separation column. The separation column contains a packing or separating medium or matrix, as well known in the art, which interacts with the various components of the sample fluid to be separated. The separation columns generally known in the art are of a cylindrical construction, the fluid flowing axially through the separating medium bed retained in the column. As the sample and elution fluids pass through the separating medium bed, the components or constituents of the sample fluid travel through the medium at different rates as a result of their differential interactions with the separation medium. Consequently, these constituents emerge separated (i.e., with different elution times and rates) in the outlet stream of the column. However, to increase the column output and to handle larger volumes, higher pressures have been found to be necessary.

More recently, the problem associated with high pressure usage, has been substantially resolved by utilizing liquid chromatographic columns witn a horizontal or radial flow through the separation medium in the column, which results in an increase in the output, using the same separation medium. Thus, higher flow rates at lower operating pressures can be achieved using the horizontal flow technique. These horizontal or radial flow liquid chromatography columns are described and claimed in copending U.S. patent application Ser. Nos. 794,727 filed Nov. 4, 1985 and 869,295 filed June 2, 1986, each in the name of Vinit Saxena.

In many applications, it is desirable to analyze and identify the chemical composition of one or more components of a sample fluid separated in a liquid chromatographic column. Such an analysis may be carried out, for example, in a mass spectrometer or by any other suitable detection device. When a mass spectrometer is used as the detection device, the fluid discharged from the liquid chromatography column must, in addition to being transported to the mass spectrometer, be rendered susceptible or amenable to the ionization thereof in the ion chamber of the mass spectrometer. Mass spectrometers are well known for their capabilities in analyzing and accurately identifying various chemicals but they also operate under high vacuum conditions, where the pressures are very low, of the order of $10^{-5}$ Torr or lower. The separated fluids discharged from the liquid chromatography columns are, most often, at atmospheric pressure or higher. In certain other applications, it would also be desirable for further separation and resolution of the effluent components, before the final analysis and identification.

Various methods and means have been designed and/or proposed for transporting the column effluent directly into the ion source of a mass spectrometer. Methods have also been proposed or designed for conditioning the column effluent for further separation and resolution of the effluent into various components, before being analyzed in the mass spectrometer while, at the same time, maintaining the integrity of the vacuum in the mass spectrometer. One such prior known means for the further separation and resolution of the components of the effluent and for conditioning it for entry into the mass spectrometer, if desired, is an electrophoresis apparatus.

Electrophoretic separations and techniques are known in the art and can provide very clean separations of many types of complex molecules in biological matrices. Typically, an electrophoretic chromatogram or electropherogram (these terms are used interchangeably herein) identifies multiple compounds as fairly discrete spots, bands or locations in an electrophoretic medium or identifies multiple compounds in an electrophoretic band or spot, but does not provide for structure elucidation or for the specific identification of individual compounds. Thus, the electrophoretic bands or spots must be prepared or conditioned for identification using a variety of transfer of staining techniques that are usually cumbersome and costly and identification is made only in terms of the electrophoretic mobilities of the unknowns in comparison with the mobilities of known standards, as is well known in the art.

More recent electrophoretic techniques utilize open tubular columns or capillaries, which allow individual derivatized or chemically tagged or isotopically labeled components to migrate past an on-line detector sensitive to or specific for the label, tag or isotope. Although this approach is sensitive, it is not specific and the compounds of interest may not be amenable to further derivatization and identification. Furthermore, dissimilar compounds may have identical or near identical migration rates and produced similar electropherograms and therefore, do not lend themselves to be differentiated.

Recently, it was discovered that when a high voltage is applied to a long, narrow bore capillary tube made of glass or quartz, an electrophoretic separation of organic, inorganic and biological compounds can be achieved. while this new capillary electrophoresis technique is being utilized for the separation and characterization of complex mixtures, it has poor sensitivity for structure elucidation and only chromatographic peaks are generated.

These prior problems of the capillary electrophoresis technique have been overcome by a new approach which utilizes capillary tubes but does not require fluorescent tags, and which operates in real time, and yields molecular weights, formulas and structural information about the compounds subjected to this new approach. This new approach is described and claimed in copending U.S. application Ser. No. 06/906,847, filed 09/15/86, 1986 in the name of Brian D. Andresen and Eric R. Fought and entitled "Electrophoresis-Mass Spectrometry Probe". With the new capillary electrophoresis technique, mixtures of chemicals, electrophoretically separated, can be directly identified by mass spectrometry.

As greater efforts are now being directed to the development of new analytical techniques and approaches, applicable to the emerging field of biotechnology, greater needs have arisen for faster and more accurate (more sensitive and specific) methods of separating biological fluids and for faster and quicker analysis of the components thereof, while minimizing the costs involved at the same time.

Therefore, it is an object of this invention to provide a means for economically separating fluids, especially biological fluids, into their various components and rapidly transporting and conditioning the components for analysis, purification or other points of use.

A further object of this invention is to provide a combined horizontal flow liquid chromatographic column and an electrophoresis apparatus for further separating and resolving the fluid components and for transporting and reducing the volume of fluids separated in tne column for substantially simultaneous (real time) analysis thereof in a mass spectrometer.

Another object of the invention is to provide a means to combine a high performance liquid chromatography column, which uses readily replaceable or separation media, with a capillary tube type electrophoresis apparatus.

Yet another object of the invention is to provide a combination of a horizontal or radial flow chromatography column and a capillary tube-type electrophoresis apparatus connected via a valved coupling wherein the separated fluid components from the column are selectively directed into the electrophoresis apparatus for conditioning therein while being transported to a point of analysis or use.

Additional objects, advantages and novel features of the invention will be set fortn in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention as embodied and broadly described herein, the present invention provides a combination of a horizontal flow liquid chromatographic column and a capillary type electrophoresis apparatus which utilizes an insertion probe. The probe is designed to be directly inserted into the ion source of a mass spectrometer. The probe also allows selected fluid components separated in the chromatographic column to be further separated and/or resolved electrophoretically for analysis in a mass spectrometer or some other device or directed to other points of use. The probe of the electrophoresis apparatus utilizes at least one capillary with high thermal conductivity walls, a heat sink, a conducting gel, and a wall coating of a nonionic, hydrophilic polymer to facilitate chromatographic separation, and is driven by a 20-30 KV potential difference. One end of the probe is open to the atmosphere while the other end may be at low vacuum, such as that used in a mass spectrometer. The electrophoresis apparatus, in another embodiment, utilizes a double capillary tube arrangement which provides for continuous operation.

The chromatographic column attached to the electrophoresis unit is of the radial or horizontal flow type, where the separation medium itself or the support member or receptacle for the medium is disposable or constructed to be readily removable and replaceable. The separation medium of the chromatographic column may, for example, be in the form of a thin wafer or matrix coated or supported on a thin glass, quartz or ceramic plate or on a thin piece of filter paper or carried on some other type of receptacle, or may be of the type wherein the medium is retained in the space between a pair of porous frits such that the medium and the frits may be removed and discarded or replaced.

The invention includes a means for directly coupling the column to the electrophoretic probe and a valving arrangement whereby fluid components discharged from the chromatographic column are controllably guided directly into the capillary tube of the electrophoresis probe. This enables substantially simultaneous (real time) analysis of fluids separated in the column, and further resolved by the electrophoresis apparatus, by means such as a mass spectrometer, fluorescence or absorption detector and the like.

DETAILED DESCRIPTION OF THE INVENTION

The present invention involves a combination of a horizontal flow liquid chromatography column and a capillary type electrophoresis apparatus, removably interconnected via a valved coupling or fluid control means, for directing material separated in the column to a point of use while conditioning or preparing fluid components in the electrophoresis apparatus for further analysis or for other use. This invention enables substantially simultaneous analysis by a mass spectrometer, for example, of fluid components separated in a chromatography column. The electrophoresis apparatus provides for further separation and resolution of the components eluted from the chromatographic column and transporting and conditioning or preparing the thus separated components for ionization in the mass spectrometer or for other points of use such as detection in a fluorescence or absorption detector. The valved coupling or fluid control means selectively injects or inserts the fluid component into a capillary tube for mixing with an electrically conducting buffer material for electrophoretic processing, as the fluid components migrate through the capillary tube in the direction of the ground terminal.

The chromatography column is preferably of a horizontal or radial flow type using readily or easily replaceable or disposable separation medium therein, and which discharges directly into the injection port of the electrophoresis apparatus.

As a result of this invention, inorganic, organic and biological compounds which are separated from complex mixtures by the column and the electrophoretic technique, can be analyzed in real time by a mass spectrometer to yield molecular weight data and structural information. Additional or alternative analytical means such as radiation, fluorescence and absorption detection instruments may be employed along with the mass spectral analysis. The electrophoresis apparatus of this invention includes an insertion probe which is chemically inert, is a good conductor of heat, as well as a good electrical insulator. The electrophoresis probe of this invention contains an electrically conducting buffer or a suitable polymer gel capable of sustaining a high voltage (20–30 KV). The construction of the column and/or the separation medium used therein is such that it enables the ready replacement or disposal of the chromatography column and/or the separation medium in the column.

The insertion probe of the electrophoresis apparatus basically comprises at least one microcapillary tube with high thermal conductivity walls connected to a heat sink, a capillary sampling port or inlet, and a wall coating of a nonionic, hydrophilic polymer to facilitate chromatographic separation, and a voltage source capable of supplying a potential difference of at least 20–30 KV. One end of the capillary tube is open to the atmosphere (at atmospheric pressure) and the other end is adapted to operate at low pressure which is close to a vacuum, and is of the order of $10^{-5}$ Torr, such as that prevailing in a mass spectrometer. Compounds (fluid components) to be electrophoretically separated are selectively injected into the insertion probe simply by turning on the high voltage at the appropriate time or via a fluid control means, such as a valve, and then allowed to migrate through the conducting buffer material towards the mass spectrometer (which is positioned between the positive and negative terminals of the voltage source) and the ground terminal. One embodiment of the probe utilizes a single capillary tube, and provides a single run or intermittent operation of the electrophoretic technique. Another embodiment employs the double capillary tube and provides for continuous operation. As used herein, whenever, the term "positively charged buffer" or buffer component is used, it is intended to mean buffer material contained in a buffer reservoir and to which is connected the positive terminal of the voltage source and is thus made positive with respect to ground. Similarly, whenever the term "negatively charged buffer" or buffer component is used, it is intended to mean buffer material contained in a buffer reservoir and to which is connected the negative terminal of the voltage source and is thus made negative with respect to ground.

Figure 1:
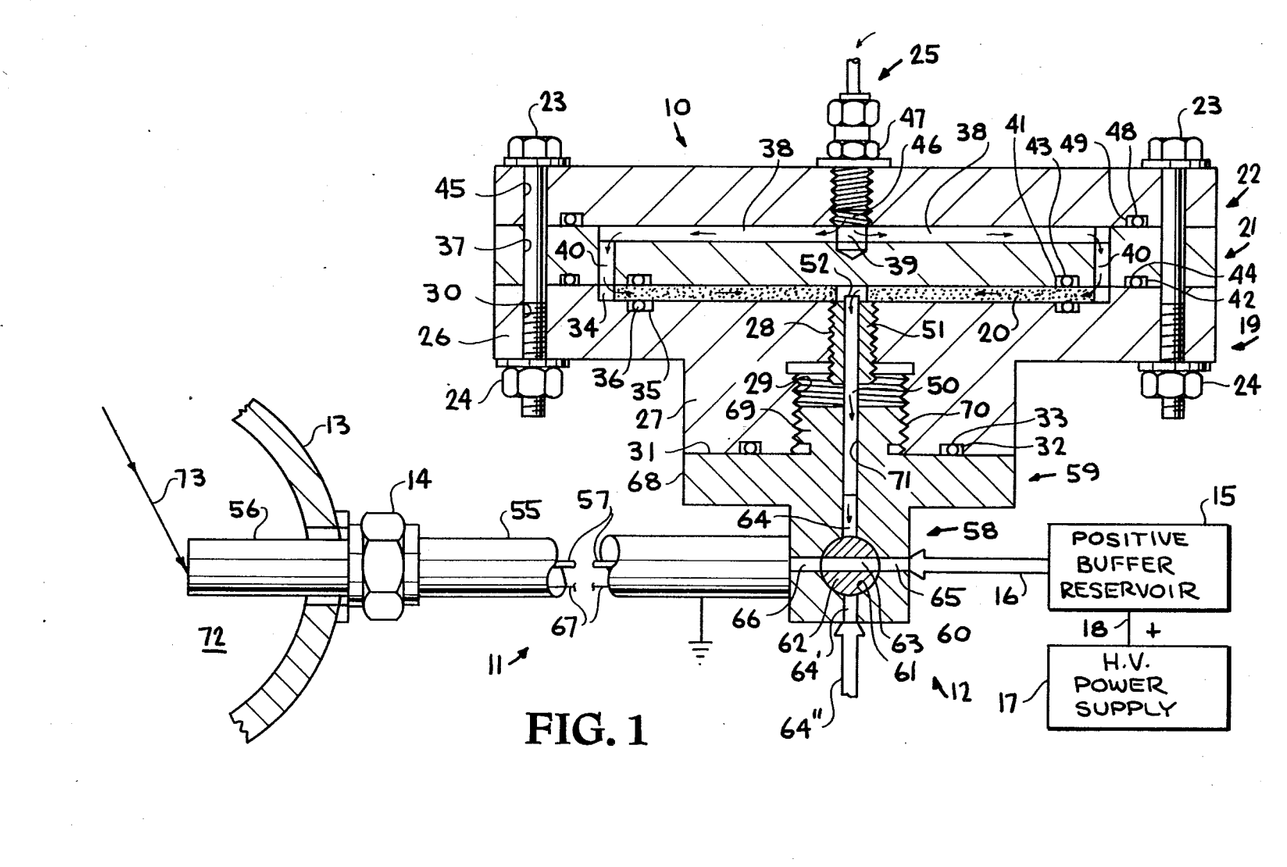
FIG. 1 illustrates an embodiment of the combination of this invention wherein the horizontal flow chromatography column is coupled to a single capillary electrophoretic apparatus via a fluid control means.

Referring now to the drawings, FIG. 1 illustrates one embodiment of the invention where a horizontal flow high performance liquid chromatography column, generally indicated at 10, is directly connected to an insertion probe, generally indicated at 11, of a single capillary electrophoresis apparatus via a fluid component introduction mechanism or control means, generally indicated at 12, with the probe 11 extending into a mass spectrometer 13 and secured therein by a coupling 14. A buffer reservoir 15 is connected to fluid control means 12 via a conduit 16, with a high voltage power supply 17 connected to reservoir 15 via an electrical lead 18 from the positive terminal of power supply 17.

The horizontal flow chromatography column 10, shown in the embodiment of FIG. 1, basically comprises a lower plate or support member 19, a wafer or thin matrix 20 of separation medium, a distributor plate or member 21, an upper plate or member 22 secured through distributor plate 21 to lower plate 19 by bolts 23 and nuts 24. A sample injection system indicated at 25 is connected to upper plate 22.

The lower plate or support member 19 comprises a body section 26 and a protruding smaller diameter section 27 having an opening extending through sections 26 and 27, and having different diameter sections indicated at 28 and 29, each opening section being threaded. Body section 26 is provided with a plurality of apertures 30 (only two shown) located in spaced relation around the periphery thereof through which bolts 23 extend. Protruding section 27 of plate 19 is provided on an outer edge or surface 31 with a groove 32 in which is located a seal 33, such as an O-ring. Body section 26 of plate 19 is also provided with a countersink 34 in which wafer 20 is positioned, and a groove 35 adjacent countersink 34 in which a seal 36, such as an O-ring, is positioned.

Distributor plate 21 may, for example, be constructed in a manner similar to the sample distribution systems described in the copending applications Ser. Nos. 794,727 and 869,825 (referenced herein earlier), and include a plurality of radially extending channels or fluid passageways. Distributor plate 21 in this embodiment is provided around the periphery thereof with a plurality of apertures 37 which align with apertures 30 in lower plate 19 and through which bolts 23 extend, and a plurality of spaced, radially extending channels or grooves 38 (only two shown) which extend outwardly from a central point 39 and form fluid distribution channels, six channels 38 being utilized in this embodiment. Distributor plate 21 is also provided with a plurality of passages 40 which extend through plate 21 and provide fluid communication between distribution channels or grooves 38 on the periphery of countersink 34 in lower plate 19. Distributor plate 21 is additionally provided with a pair of grooves 41 and 42 located on opposite sides of and spaced from the passages 40 in which are located seals or O-rings 43 and 44, respectively.

Upper plate 22 is provided with a plurality of apertures 45 positioned around the periphery so as to align with the apertures in distributor plate 21 and lower plate 19, through which bolts 23 extend. Threaded opening 46 is located in the center of plate 22 and is in alignment with central point 39 of distributor plate 21. A fitting or coupling indicated at 47 is secured in opening 46 and connected to sample fluid injection system generally indicated at 25. A groove 48 is formed on a lower surface of upper plate 22 in alignment with grooves 42 of distributor plate 21, and in which is located a seal 49, such as an O-ring.

A fluid sample component discharge tube 50 is secured at one end by a threaded member 51 secured in threaded opening section 28 of lower or support plate 19 and extends outwardly through opening section 29 of plate 19, and is positioned so as to deposit separated fluid components discharged from column 10 into fluid control means or fluid component introduction means 12, as described hereinafter.

With the components of chromatography column 10 positioned as shown in FIG. 1, sample and elution fluids are injected into column 10 from system 48 via opening 46 in upper plate 22 and travel outwardly through distribution channels or grooves 38, through passages 40 into the periphery of countersink 34 in lower plate 19, whereafter the sample and elution fluids pass horizontally or radially inward through separation material wafer or matrix 20. The sample is separated into various constituents or components as it traverse through the separation medium, which then pass into a central opening or collection channel 52 and discharge through tube 50, as indicated by the flow arrows. The constituents or components of the sample fluid separated within or on the wafer or matrix 20 emerge at different times into collection channels 52, as the different components normally have different elution rates and times, as known in the art. For a further description of the operation of a radial or horizontal flow chromatographic column, if such is desired, reference is made to the previously referenced copending applications of V. Saxena (U.S. Ser. Nos. 794,727 and 895,295).

The wafer or matrix 20 of separation medium may, for example, have a diameter of 1" to about 6" a thickness of 0.010 to about 0.100 mils (or 100 to about 2000 microns), and composed of any suitable separation medium known in the art, which include but not limited to ion exchange resins, cellulosic materials, agarose, sepharose and the like, deposited or coated as a thin layer on a suitable support member or receptacle such as a thin glass, quartz or ceramic plate, or a piece of filter paper and the like. The choice of the separation medium depends on the sample or fluid component material desired to be separated in the column 10, as is known in the art.

As can be seen, the column 10 can be readily disassembled to interchange or replace the separation medium 20 or the entire column 10 can be quickly and easily removed from the fluid control means 12 and another column installed in its place if desired.

The insertion probe 11 of the electrophoresis apparatus comprises a casing or housing 55 having tip section 56 located within mass spectrometer 13 and secured thereto by coupling mechanism 14, a capillary tube 57 extending through casing 55 and into sample introduction or fluid control mechanism 12. Sample introduction or fluid control mechanism 12 includes a multi-port valve section 58 and column coupling or connector section 59 connected to valve section 58, with sections 58 and 59 being illustrated in enlarged cross-section. Valve section 58 comprises a housing 60 having a chamber 61 therein in which a rotatable member 62 is positioned, member 62 having a passage 63 extending therethrough. Housing 60 is provided with four ports or passages 64, 64', 65 and 66 with port 64 being connected to tube 50 from column 10, port 64' being connected to line, tube or conduit 64", port 65 being connected to line, tube or conduit 16 which is connected to buffer reservoir 15, and port 66 being connected to capillary tube 57. Line, tube or conduit 64" may be, in turn, provided with a transparent, quartz or glass window and connected to an additional detection or monitoring means for continuously monitoring or detecting the eluting compounds from column 10, or may be connected to a disposal means or unit for the excess effluent from column 10. The rotatable valve member 62 is connected to an activation and timing mechanism, not shown, for rotating member 62 at a selected interval between the position shown where passage 63 is aligned with ports 65 and 66 for allowing buffer material or fluid from reservoir 15 to pass into capillary tube 57, to a position where passage 63 is aligned with port 64 which allows the passage 63 to be filled with fluid components or sample material discharged from column 10. when the passage 63 is filled with sample material, the valve 62 is rotated to the position shown whereby the sample material in passage 63 is mixed with buffer material from reservoir 15, and undergoes electrophoretic separation as it migrates down capillary tube 57.

Electrical energy for the electrophoretic process is supplied by power supply 17 (20–30 KV) with a positive terminal thereof connected by electrical lead 18 to buffer reservoir 15, making it positive with respect to ground. An electrical lead or return line 67 is connected to the negative terminal of power supply 17 via a grounded connection. Return electrical lead 67 is electrically connected to capillary tube 57 as shown in FIG. 2 of copending application Ser. No. 906,847 referred to herein.

Section 59 of sample introduction or fluid control mechanism 12 comprises a body section 68 and a protruding reduced diameter portion 69 having threads 70 on the outer surface. Body portion 68 may be integral with or secured to housing 60 of valve section 58. An opening 71 extends through section 59 and aligns with port 64 and into which tube 50 extends. Threads 70 cooperate with threaded aperture 29.

Components of the sample material from column 10, after undergoing the electrophoretic separation as the materials migrate down the capillary tube 57, are ionized and discharged from the probe tip section 56 of casing 55 into an ion source or chamber 72 of mass spectrometer 12. As the components reach the probe tip, they are subjected to bombardment by high energy, ionizing beam 73 or other ionizing means, such means including but not limited to fast atom or electron gun bombardment, electrospraying and surface ionization and other techniques known in the art. The migrating components on the probe tip are thereby ionized and guided into the ion source of the mass spectrometer 13 where they are then analyzed and identified. The beam 73 which may be composed of xenon gas, for example, is preferably directed onto the components on the tip 57 of the probe at an angle between 45° and 90°. Coupling mechanism 14 provides a vacuum tight connection between casing 55 and mass spectrometer 13.

Capillary tube 57 is secured in casing 55 by means not shown, and, in this embodiment, is of a multi-layer configuration consisting of a central tube, an inner layer and an outer layer as illustrated and described in FIG. 2 of the above referenced copending application Ser. No. 06/906,847. The central tube may be constructed of quartz, glass, ceramics, sapphire and the like, for example, having an internal diameter of about $5\mu$ to about $100\mu$, and wall thickness of about 50 mils to about 200 mils. The inner layer may be composed of plastic, acrylic, teflon, polycarbonate, polyacetate, polysulfone, polysilicates and the like with a thickness of about 0.01 mils to about 0.50 mils, and an inner diameter of about $5\mu$ to about $100\mu$. The outer layer may be constructed of an inert material such as stainless steel, aluminum, quartz, ceramic and the like, with a thickness of about 0.5 inch to about 1 inch. The protective layers on the central tube of capillary tube 57 function to electrically insulate the probe tip and the capillary tube which must "float" with respect to the ground potential of the mass spectrometer so that the ion optics of the mass spectrometer are not defocused or grounded out during probe insertion. This mode of construction allows compounds to travel down the capillary tube towards the ion source of the mass spectrometer. The very tip of the capillary is made negative with respect to the high voltage anode side of the electrophoresis capillary. Chemicals travel to the tip fully separated. These electrophoretically pure chemicals sputter off the tip of the capillary tube directly into the ion source of the mass spectrometer. This type of analysis enables one to obtain molecular weights and structural information about a great many polar and sophisticated chemicals which would not be easily identified by electrophoresis alone.

While the single capillary electrophoresis system of FIG. 1 is easy to set up, operate and maintain for short period of time and works well for single runs, it has to be cleaned and reconditioned each time an analysis is performed because the tip of the tube heats up and dries out over each run and has to be cleaned before further use. Furthermore, with successive or consecutive runs, since the probe tip gets very near the ion source of the mass spectrometer, which is typically heated to a temperature of 200° C., and is also bombarded with high ionizing energy beams, these two events contribute additional energy and raises the temperature of the probe tip. This then heats up the buffer and the polymer at the end of the probe tip. when the buffer and the polymer at the end of the probe tip become too hot, electrical conduction through the buffer is lost, current flow therethrough diminishes as a result, and electrophoretic separation process slows significantly. The single capillary tube of FIG. 1, however, works satisfactorily for single or intermittent runs, can be manufactured inexpensively and can, therefore, be made disposable and discardable after each run.

Figure 2:
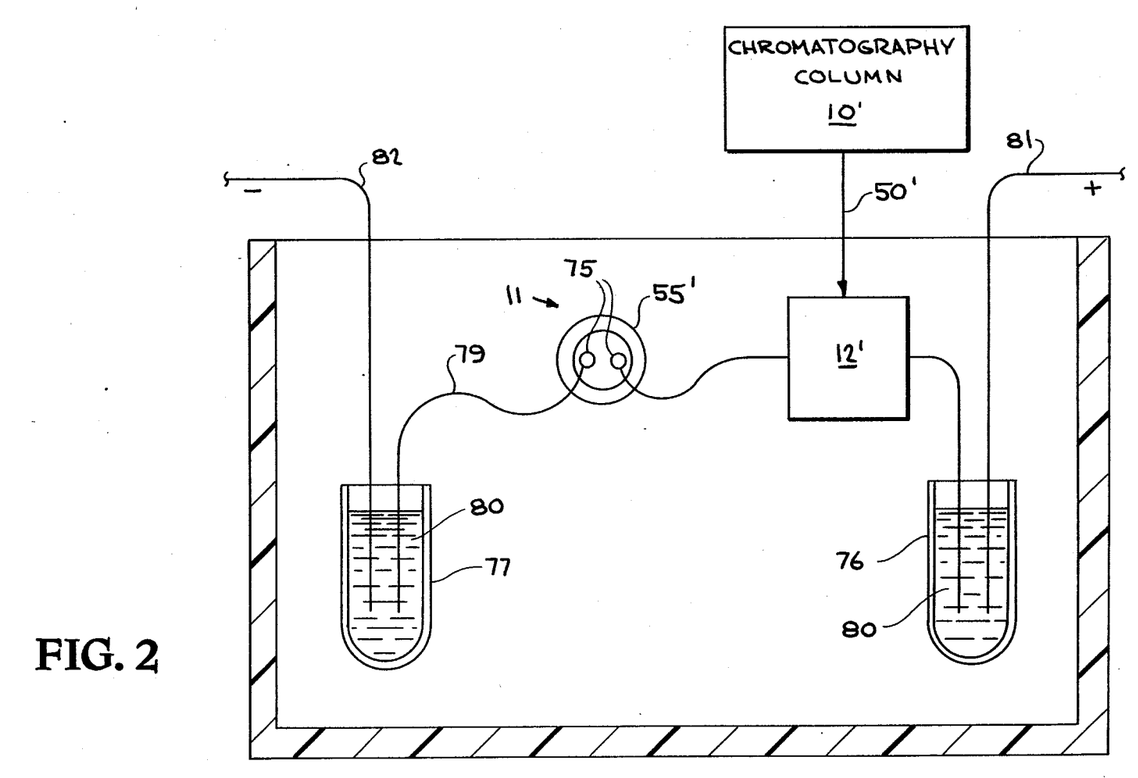
FIG. 2 schematically illustrates the relationship of the electrophoresis probe, a chromatography column, sample introduction means and buffer reservoirs, wherein the probe is of a double capillary tube.
Figure 3:
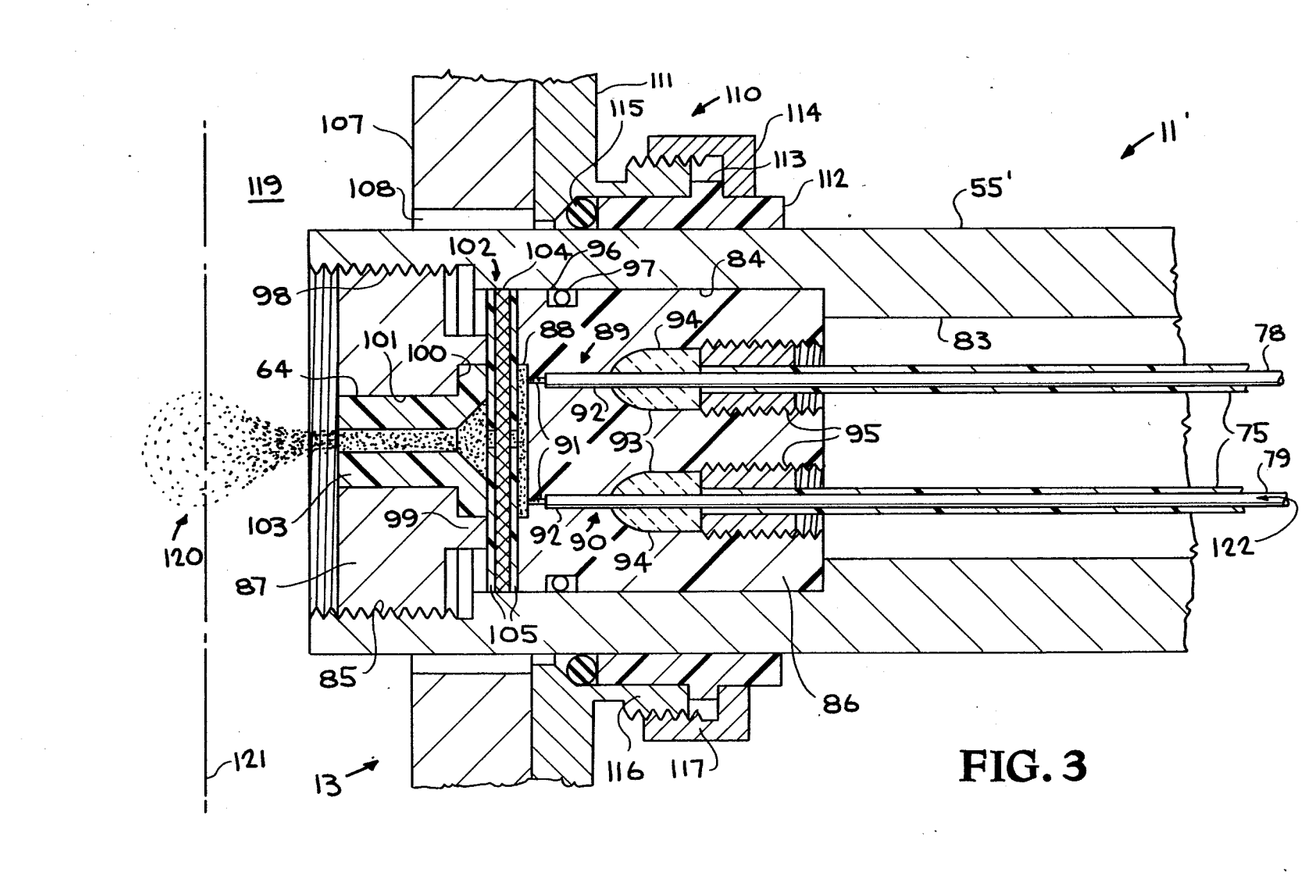
FIG. 3 is an enlarged view of the probe tip of a double capillary electrophoresis apparatus.

The double capillary indicated at 11' in FIGS. 2 and 3 overcomes the problems of the single capillary tube of the embodiment shown in FIG. 1, and provides for continual operation. This double-feed-line approach allows for the capillary electrophoresis probe tip to be continually wetted by the buffer, thereby preventing the drying up of the buffer components on the probe tip. Tnis also allows for increased heat dissipation and results in a continually operating probe which is more durable and electrically more stable. As described below, the double capillary probe tip includes a "cell" located near the end and within the mass spectrometer and thus is subjected to heat from the the ion source as well as bombardment by beams of high ionizing energy. Although a variety of materials such as teflon, polyvinyl chloride (PVC), stainless steel, glass, polyethylene, Viton, polycarbonate, and a combination of these materials are suitable for the construction of the "cell", polycarbonate is the preferred material because of its strength, electrical insulation capabilities and its ability to be machined into small parts. The probe tip has a diameter of about 0.5 inch and a length of about 1 inch, for example, with the probe having an overall length of about 12 to 14 inches.

FIG. 2 schematically illustrates the relationship between a high voltage power supply (not shown), a pair of buffer reservoirs 76 and 77, sample insertion or fluid control 12', column 10' connected to fluid control 12' via tube or conduit 50' and a pair of capillary tubes 78 and 79 located in probe casing 55' via sleeves 75. As shown in FIG. 2, each of the buffer reservoirs 76 and 77 is filled with an electrically conducting buffer material or fluid 80, such as phosphate, citrate, tris-HCl and the like, known in the electrophoresis art. Buffer reservoir 76 is connected to a positive terminal of a power supply such as the one indicated by the numeral 17 in FIG. 1, via an electrical lead 81, while an electrical lead 82 connects buffer reservoir 77 with a negative terminal of the power supply. Probe casing 55' is mounted on the mass spectrometer (not shown) as described and illustrated hereinafter in the discussion of the double capillary tube probe embodiment shown in FIG. 3.

By way of example, the capillary tubes 78 and 79 may be constructed of quartz, sapphire, ceramic, glass and the like and may have an inner lining as described earlier for the embodiment of FIG. 1. Also as an example, when the material from column 10' is a protein, and the buffer in reservoir 76 is 0.05 N $NaH_2PO_4$, approximately 1–10 mg of the sample material is directed into capillary tube 78 within a time period of about 10–15 min.

An embodiment of the double capillary tube described and claimed in the earlier referenced copending application Ser. No. 06/906,847, is illustrated in FIG. 3 and described hereinafter. The probe tip of FIG. 3 comprises a housing or casing 55', constructed of stainless steel, for example, with an outside diameter of about 0.5 inch. The capillary tubes 78 and 79 extend into casing 55' within electrical insulation sleeves 75, constructed of polyurethane, for example, with a wall thickness of 0.10 inch. Housing or casing 55' is provided with a longitudinally extending opening having three different diameter sections 83, 84 and 85. A capillary terminal block 86 or "cell" discussed above is positioned in section 84 of casing 55', while a retainer plug or member 87 is positioned in section 85 of casing 55'.

Capillary terminal block or "cell" 86 is preferably constructed of polycarbonate and is provided with an elongated slit, groove, or countersink portion 88, having a width of about 0.010 inch to about 0.10 inch at one end thereof with a pair of spaced passageways 89 and 90 extending from the opposite end into slit or countersink 88, as seen in FIG. 3A. Passageways 89 and 90 each is provided with three different diameter section 91, 92 and 93, with sections 93 having a tapered or curved inner portion and a threaded outer portion. Capillary tubes 78 and 79 extend through opening section 83 of casing 55', through sections 93 of passageways 89 and 90 and into sections 92, so as to terminate adjacent sections 91 of the passageways. A pair of graphite seals 94 are positioned in the curved end portions of passageways sections 93 and around capillary tubes 78 and 79. The seals 94 may be constructed of graphite or teflon for example. The insulation sleeves 75 terminate in passageway sections 93 adjacent the seals 94 with the seals 94 being held in place by threaded retainer members or plugs 95, which may be constructed to also retain the inner end of the insulation sleeves 75. Retainer members 95 may be constructed of stainless steel or hard plastic, for example. Capillary terminal block 86 is also provided with a groove 96 which extends around the periphery thereof and in which is located a seal member 97, such as on O-ring, which provides a vacuum seal between the inner surface of casing 55' and block 86. The elongated slit 88 in block 86 may be enlarged to an oval configuration, which would increase sensitivity but reduce resolution of the material components passing therethrough.

Retainer plug or member 87 is provided with external threads 98 which cooperate with threads on the casing open end section for removably retaining plug 87 in casing 55'. Retainer plug 87 includes a reduced cross-section protruding portion 99 having a countersink 100 therein which is connected to a centrally located opening 101 which extends through plug 87. Protruding portion 99 of plug 87 extends into casing open end section and serves to retain a screen assembly, generally indicated at 102, in abutment with capillary terminal block 86. A nozzle 103, constructed of plastic or other suitable material, is positioned in countersink 100 and opening 101 of retainer plug 87 and abuts against the screen assembly. The screen assembly 102 comprises a molecular screen or sieve 104 positioned between a pair of spacers or washers 105 having centrally located apertures 106. The molecular screen 104 may, for example, be constructed of polycarbonate, teflon, or cellulose with a thickness of about 0.050 inch to about 0.100 inch, with the washers 105 being constructed of teflon, metal, or polycarbonate, having a thickness of about 0.010 inch to about 0.050 inch, with the apertures 106 having a diameter of 0.10 inch. The screen assembly 102 is pressed against the face or end of block 86 by retaining plug 87 being threaded into casing section 55' to produce a tight fit therebetween.

Mass spectrometer 13' includes a wall 107 having an opening 108 therein through which an end of probe tip casing 55' extends, as seen in FIG. 3. The casing 55' is retained in wall 107 by a coupling mechanism generally indicated at 110, which includes a collar or mounting member or bracket 111 constructed of stainless steel, brass, aluminum or any similar durable material, for example, and secured to wall 107, by means not shown, such as by welding or screws; an electrical insulation sleeve or member 112, constructed of polystyrene, teflon or insulating plastic, for example, positioned around casing 55', sleeve 112 having a protruding section or ring 113; a seal nut or bracket 114 positioned around sleeve 112; and an O-ring 115 positioned around casing 55' intermediate mounting member 111 and sleeve 112. Mounting member 111 includes an outwardly extending flange portion 116 which fits around sleeve 112 and has an external threaded surface. Seal nut 114 includes an outwardly extending flange portion 117 having an internal threaded surface which cooperates with the threads on flange portion 116 of mounting member 111. Turning of the seal nut 114 onto the mounting member 111 contacts the protruding ring 113 of sleeve 112 forcing sleeve 112 toward O-ring 115 and mounting member 111, causing a vacuum tight seal between probe casing 55' and mass spectrometer wall 107 while mounting or securing casing 55' to wall 107.

In operation of the FIG. 3 probe, sample material from column 10' of FIG. 2, which is separated into components in capillary tube 78 by the electrophoresis process, is directed from capillary tube 78 via passage 91 into slit 88 where it is vaporized, and then passes through opening 106, through a first washer 105, through molecular screen 104, opening 106 in the other washer 105, and through nozzle 103 into a chamber 119 of mass spectrometer 13' as indicated at 120. The components 120 of the sample material are struck by an ionizing beam 121, such as ionized xenon gas, for example, from a fast atom, electron or photon bombardment gun, not shown.

To maintain continuous operation of the FIG. 3 probe tip electrically conducting buffer material or fluid 80 from buffer reservoir 77 migrates through capillary tube 79 as indicated at 122 into passage 91 and slit 88. This prevents the tip or end of capillary tube 78 from heating up and drying out, as discussed above with respect to the single capillary probe tip of the FIG. 1 embodiment, thereby conduction through the buffer is maintained, current flow is not diminished, thus enabling continual operation of the electrophoresis process. The negatively charged material 122 passing through capillary 79 also serves to complete an electrical circuit from and to the power supply.

Figure 4:
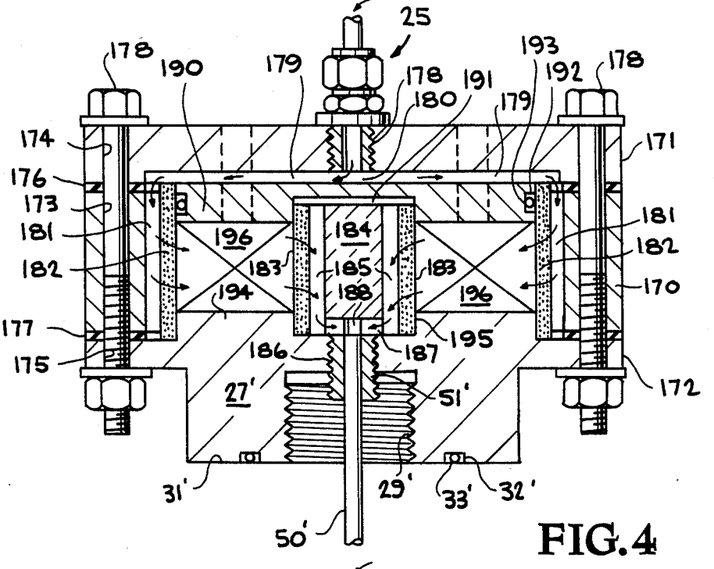
FIGS. 4 and 5 illustrate other embodiments of horizontal or radial chromatography columns of the combination which utilize a disposable separation medium retained between porous frits.

Referring now to FIG. 4 which illustrates another embodiment of a replaceable horizontal or radial flow column, and/or replaceable or disposable separation medium in said column, mounted on or to the housing of the electrophoresis apparatus as shown in FIG. 1. This column differs from the column of FIG. 1 primarily in the use of the separation material being retained between two spaced porous frits rather than being fabricated as a wafer or held on a supporting matrix. Components which correspond to those illustrated in FIG. 1 are given corresponding reference numerals. The column is composed of a cylindrical body section 170, an upper end cap, plate or section 171 and a lower end cap, plate or section 172. Body section 170 is provided with a plurality of spaced openings or apertures 173 (only two shown), while end caps 171 and 172 are provided with a plurality of openings or apertures 174 and 175 respectively, which correspond to and align with openings 173. A pair of annular seals or gaskets 176 and 177 having openings which align with openings 173 are positioned between body section 170 and end caps 171 and 172. Bolts 178 (only two shown) extend through openings 173, 174 and 175 and gaskets 176 and 177 for securing housing components 170, 171 and 172 together.

As in the embodiment of FIG. 1, upper end cap or plate section 171 is provided with a threaded fluid inlet passage or opening 178 which directs fluid from a source via a coupling 25 to a plurality of distributor grooves or channels 179 (only two shown) via a central point 180, and grooves 179, terminating adjacent to and providing fluid communication with an annular, longitudinally extending channel 181 formed between an outer porous frit 182 and body section 170. An inner porous frit 183 is snugly positioned around a solid core or member 184 having longitudinally extending grooves or channels 185 (only two shown). The grooves 185 of core 184 are connected to a threaded outlet or collection passage 186 in lower end cap or plate 172 via a plurality of radially extending passages 187 and a central passage 188 in the lower end of core 184. The solid core or member 184 may be constructed, for example, as illustrated in detail in FIG. 4 of the previously referenced copending application Ser. No. 869,295.

A support plate or member 190 having a central counter-sunk portion 191 and an annular groove 192 for retaining a seal such as an O-ring 193 which is positioned to cooperate with outer frit 182, with inner frit 183, and with solid core 184. Support plate 190 is retained, as shown in FIG. 2, by upper end cap 171.

Lower end cap or plate section 172 is provided with an inwardly protruding section 194 which includes a counter-sunk portion 195 into which ends of inner frit 183 and solid core 184 are positioned, with outer frit 182 extending around protruding section 194. A bed 196 of a selected separation medium is retained or located between porous frits 182 and 183, with outer frit 182 being retained between end caps 171 and 172, while inner frit 183 is retained between support plate 190 and lower end cap 172.

In operation of the column of FIG. 4, a sample fluid followed by an elution fluid from a sample injection system 25 enters inlet passage 178 and flow outwardly through channel 179 to various points around channel 181, whereafter the fluids pass radially or horizontally inward through outer porous frit 182 and through separation medium bed 196 where the sample fluid is separated into components. The separated components then pass through inner frit 183 into grooves 185 of solid core 184, whereafter the fluid components pass through passages 187 and passages 188 into outlet or collection passage 186 in which one end of a tube 50' is retained by a threaded coupling 51' similar to that shown in the embodiment of FIG. 1.

To provide for attachment of the chromatography column of FIG. 4 onto the fluid control or fluid component introduction means 12, as shown in FIG. 1, lower end cap or plate section 172 includes an outwardly protruding, smaller diameter portion 27' (as in the FIG. 1 embodiment), having a threaded opening or aperture 29' through which tube 50' extends for connection with sample introduction means 12, as in FIG. 1. Protruding section 27' is provided on an outer edge 31' with a groove 32' in which is retained a seal or O-ring 33'.

Thus it is seen that the column of the type illustrated in FIG. 4 has been designed for ready replacement or disposal and is readily attachable and removable from the sample introduction means 12. Furthermore, the separation medium bed 196 of the FIG. 4 column can be easily replaced by removal of the retaining bolts 178, upper end cap 171 and support plate 190, whereby the bed 196 and, if desired, the porous frits 182 and 83 can be easily removed for cleaning purposes or replaced. The bed and frits together or even the entire column may also be fabricated as a prepacked, integral, disposable unit.

If desired, the outer frits 182 may be provided with a plurality of spaced, longitudinally extending grooves on the outer surface thereof, such that the fluid distribution channels or grooves 179 are in fluid communication therewith. The upper and lower end caps or plate sections 171 and 172 may also be secured to column body section 170 via short screws instead of bolts 178 such that either of the end caps 171 or 172 can be independently or individually removed while leaving the other end cap secured to body section 170. Head bolts 178 and their nuts or substitute screws may also be counter-sunk to give the top surface a smooth contour, thereby facilitating a stacking of the columns in series or in parallel when a greater resolution or greater throughput is desired as the case may be. In a series connection, the collection output of one column is fed into the material entrance passage of the next column. In such a series set up, any specific material desired to be separated may be arranged to be siphoned off at any stage. In a parallel connection, a sample splitter would feed the sample simultaneously to the sample entrance ports of the stacked columns, so that the effluents from all the stacked columns are pooled and collected together to yield a greater throughput.

Figure 5:
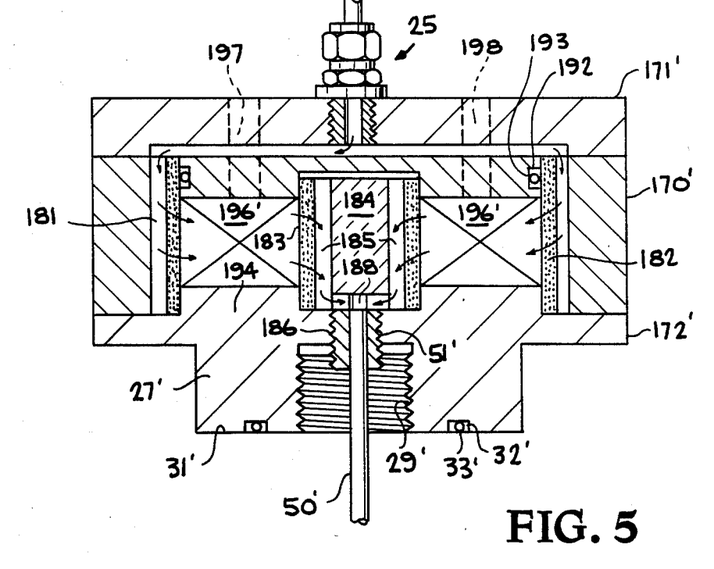

FIG. 5 illustrates an embodiment which is generally similar to the FIG. 4 column, with the principal difference being in the fabrication of the entire column and in the manner of securing the housing components of the column together so to make the entire column and the separation material therein prepacked and disposable. In the embodiment of FIG. 5, the housing components, the porous frits, and the separation medium are made of selected, cost-effective materials and are constructed to be integral or sealed (glued, bonded or molded) together such that after use, the entire column together with the prepacked separation medium, may be discarded.

In FIG. 5, like components or components similar to those shown in FIG. 4, are given corresponding reference numerals. In FIG. 5, the housing is composed of a cylindrical body section 170', an upper end cap or section 171', and a lower end cap or section 172'. The end cap 171' and 172' are constructed so as to be in abutting relationship with body section 170' and are secured together such as by welding, bonding, gluing, molding and the like, thereby eliminating the gaskets 176, 177 and bolts 178 of the embodiment of FIG. 4. This type of construction also eliminates a great deal of machining requirements, thereby reducing the cost of fabrication considerably. The remainder of the column of FIG. 5 is the same as that of FIG. 4 except that the upper end cap 131' and plate member 190 are provided with a pair of spaced and aligned apertures 197 and 198, which allow for insertion of the separation medium to form a bed within the housing and for the removal of any trapped air within the housing.

The operation of the column of FIG. 5 is substantially the same that of the embodiment of FIG. 4, the only difference being in that the entire column of FIG. 5 is disposable after use. The column housing of the embodiment of FIG. 5 is constructed out of relatively inexpensive materials, and the components 170' and 171' or 172' may all be initially integrally molded with the other end cap 171' and 172' being bonded or glued. Thereafter, the porous frits and core member are positioned within the housing, the separation bed material retained between the frits being injected through one of the openings, ports or apertures 197 or 198, with any trapped air being removed through the other opening 197 or 198. The openings 197 and 198 are sealed (as by gluing, bonding etc) during the operation of the column.

The materials utilized in the illustrated embodiments of the above described chromatography columns may be the same as those described in the earlier referenced copending application Ser. No. 794,727. For example, the column housing and other non-filtering components may be constructed out of materials capable of withstanding extreme solvent and temperature conditions, such materials including but not limited to stainless steel, aluminum, titanium, glass, ceramics, quartz, teflon, polycarbonate, polysulfone, polypropylene, polyethylene, and the like. Similarly, the porous frits may be made of polyvinylidene fluoride (PVF), polypropylene, polyethylene, teflon, stainless steel, polyacetate, polyester, polycarbonate, ceramics, and such other porous materials as are known in the art. The separation bed material or medium may be composed of any separation material known or employed in the art of chromatographic separations and is dependent on the materials desired to be separated.

It has thus been shown that the present invention enables substantially simultaneous analysis in a mass spectrometer or other similar device, of fluid components separated in a liquid chromatography column, which are further separated or resolved by capillary zone electrophoresis. The combination of a readily removable and/or disposable column and an electrophoresis apparatus, provided by this invention, in the form of a compact, portable, integral unit, greatly advances the state of the technology in the area of rapid and accurate analysis of various types of separated components in body and other fluids of biological interest. Furthermore, the electrophoresis apparatus further resolves or conditions the sample material for further analysis while transporting the same from the column to a point of use or detection. Thus this invention enables the separation, transport, conditioning, detection and analysis of polar and/or biological compound from complex mixtures.

While a particular embodiment of the invention and specific materials and parameters have been illustrated and described for purposes of illustration and to provide a better understanding of the invention, it is not intended to be exhaustive or to limit the invention to the particular illustrations or embodiments so described. The above embodiments were chosen and described in some detail in order to explain best the principles and the practical application of the subject invention thereby to enable those skilled in the art to utilize the invention in various other embodiments and various modifications as are suitable for the particular use contemplated. Obviously many modifications and variations are possible in light of the above teaching. It is intended that the scope of the invention be defined by the claims appended hereto.

What is claimed is:

1. A system for separating fluid components and conditioning at least certain of the components for analysis or other use, comprising the combination of:
   a horizontal flow liquid chromatography column;
   a capillary type electrophoresis apparatus; and
   means for interconnecting said column with said electrophoresis apparatus and controlling flow of fluid components from said column into said electrophoresis apparatus;
   said column being removably mounted on said means such that associated fluid components separated in said column are controllably deposited directly into said electrophoresis apparatus, said column including disposable fluid separation material, and a fluid distribution and component collection system in which associated fluid to be separated is adapted to be directed around at least a portion of one of side of the fluid separation material and directed radially through the fluid separation material with separated fluid components being collected at an opposite side of the fluid separation material for discharge into said means;
   said electrophoresis apparatus including at least one capillary tube operatively connected to said means, a reservoir for electrically conducting buffer material operationally connected to said means, and means for connecting a positive terminal of a high voltage source on buffer material contained in said reservoir;
   said means including a multi-port valve assembly operationally connected to said component collection system of said column to said capillary tube and to said buffer material reservoir, for selectively directing associated fluid components and associated buffer material into said capillary tube.

2. The combination of claim 1, said means additionally includes an externally threaded member secured to said valve assembly for threaded, removable interconnection with an internally threaded member on said column, and means extending through said threaded members for interconnecting said component collection system of said column with said valve assembly.

3. The combination of claim 2, wherein said externally threaded member comprises a first section secured to said valve assembly and having an outer surface, and a second section having a smaller cross-section than said first section ano protruding outwardly from said surface of said first section and provided with external threads, a fluid passageway extending through said first and second sections of said externally threaded member, said externally threaded protruding section of said member being connected to said internally threaded member of said column, said interconnecting means extending into said fluid passageway of said externally threaded member.

4. The combination of claim 3, wherein said internally threaded member of said column comprises a lower support member having a first section with one side thereof in abutment with the fluid separation material of said column and provided with a substantially centrally located opening, a second section of smaller cross-section than said first section and protruding outwardly from said first section and provided with a substantially centrally located threaded opening and an outer surface having a sealing means therein, said threaded opening of said section cooperating with said threaded protruding section of said externally threaded member such that wnen said threaded sections are threadedly interconnected, said outer surfaces of said members are in contact with eacn other and said sealing means preventing fluid leakage between said members, said interconnecting means extending through said openings in said lower support member and being connected at one end in said opening of said first section of said lower support member.

5. The combination of claim 4, wherein said opening of said first section of said lower support member is provided with threads, wherein said interconnecting means comprises a tube, and including threaded means for securing one end of said tube in said threaded opening of said first section.

6. The combination of claim 1, wherein said multi-port valve assembly includes:
   a housing having a chamber therein,
   a member movably located in said chamber of said housing, said member being provided with a passage extending therethrough,
   said housing being provided with a plurality of ports extending from an outer surface to said chamber, one of said ports being operationally connected to said component collection system of said column, another of said ports being operationally connected to said capillary tube, and another of said ports being operationally connected to said buffer material reservoir,
   whereby movement of said member in said housing chamber aligns said passage therein with said component collection system or with said capillary tube and said buffer material reservoir.

7. The combination of claim 6, wherein said means additionally includes a connector member secured to said housing of said multi-port valve assembly, said connector member including first and second sections, with said second section being of smaller cross-section than said first section and protruding outwardly from a surface of said first section, said protruding second section being provided with threads, and a fluid passageway extending through said first and second sections and aligned with said one of said ports of said valve assembly housing.

8. The combination of claim 7, wherein said column includes a support member having an opening therein in alignment with said fluid passageway of said connector member, said opening including a threaded section for threaded interconnection with said protruding second section of said connector member, said support member also including an outer surface adapted to contact said outer surface of said first section of said connector member, and sealing means positioned between said outer surfaces.

9. The combination of claim 8, additionally including interconnecting means between said component collection system of said column and said connector member, said interconnecting means being secured at one end of said opening in said support member and extending into said fluid passageway of said connector member.

10. The combination of claim 9, wherein said opening in said support member additionally includes another threaded section, wherein said interconnecting means comprises a tube, and wherein one end of said tube is secured by a threaded member in said another threaded section of said opening in said support member.

11. The combination of claim 1, wherein said separation material of said column is in the form of a wafer.

12. The combination of claim 1, wherein said separation material is positioned intermediate a pair of spaced porous frits.

13. The combination of claim 1, wherein said column is of a disposable type.

14. The combination of claim 1, wherein said electrophoresis apparatus includes a pair of capillary tubes, a first of said capillary tubes being operationally connected to said multi-port valve assembly, a second of said capillary tubes being connected to another reservoir for electrically conducting buffer material, and a power supply having a positive terminal thereof being connected to said first mentioned reservoir and a negative terminal thereof being connected to said another buffer reservoir.

15. The combination of claim 14, wherein said pair of capillary tubes are at least partially located in spaced relation within a casing, each of said capillary tubes extending into and terminating at one end in passageways in a support block positioned in said casing, said support block also having a groove extending between said passageways therein.

16. The combination of claim 15, additionally including a molecular sieve assembly positioned in said casing and closely adjacent said groove in said support block, and means for retaining said molecular sieve assembly in said casing 17. The combination of claim 15, wherein an end of said casing in which said molecular sieve is located is positioned within a chamber of a mass spectrometer, and additionally including means for removably securing said casing in said mass spectrometer in a vacuum tight arrangement.

18. The combination of claim 1, wherein at least a portion of said capillary tube is positioned within a casing and connected at one end to said multi-port valve assembly, another end of said capillary tube terminating adjacent an end of said casing, and means for electrically connecting said another end of said capillary tube to an electrical ground, said end of said casing being adapted to be located at a point of use of said electrophoresis apparatus.

19. The combination of claim 18, wherein said end of said casing is secured in a mass spectrometer in a vacuum tight relationship.

20. In a system consisting of a liquid chromatography column, an electrophoresis apparatus, and a mass spectrometer, the improvement comprising:

means for removably connecting at least one chromatography column directly to an electrophoresis apparatus through a valve assembly connected to at least one reservoir for containing electrically conducting buffer material and connected to a capillary tube of said electrophoresis apparatus, and means for connecting said electrophoresis apparatus to said mass spectrometer in a vacuum tight relationship, said chromatography column being of a horizontal flow type, whereby movement of said valve assembly to a first location allows fluid components separated in said column to be directed through said connecting means into said valve assembly, and movement of said valve assembly to a second location allows buffer material from said reservoir to pass through said valve assembly and direct the fluid components therein into said capillary tube in which fluid components undergo conditioning by electrophoresis as the components and buffer material pass through the capillary tube.

21. The improvement of claim 20, wherein said chromatography column is of a disposable type.

22. The improvement of claim 21, wherein said chromatography column is constructed so as to be readily disassembled and contains a disposable separation medium.

* * * * *